(12) United States Patent
Bhattacharjee (10) Patent No.: US 10,080,558 B2
(45) Date of Patent: Sep. 25, 2018

(54) DEVICE PROVIDING ENLARGEMENT AND PREVENTING COLLAPSE OF THE PUPIL OF THE EYE

(71) Applicant: Suven Bhattacharjee, Kolkata (IN)

(72) Inventor: Suven Bhattacharjee, Kolkata (IN)

(73) Assignee: MED INVENT DEVICES PRIVATE LIMITED, Kolkata, West Bengal (IN)

( * ) Notice: Subject to any disclaimer, the term of this patent is extended or adjusted under 35 U.S.C. 154(b) by 71 days.

(21) Appl. No.: 14/379,684

(22) PCT Filed: Jul. 23, 2013

(86) PCT No.: PCT/IN2013/000457
§ 371 (c)(1),
(2) Date: Aug. 19, 2014

(87) PCT Pub. No.: WO2014/132264
PCT Pub. Date: Sep. 4, 2014

(65) Prior Publication Data
US 2015/0351736 A1 Dec. 10, 2015

(30) Foreign Application Priority Data
Feb. 27, 2013 (IN) .............................. 225/KOL/2013

(51) Int. Cl.
*A61B 17/02* (2006.01)
*A61B 17/00* (2006.01)

(52) U.S. Cl.
CPC ...... *A61B 17/0231* (2013.01); *A61B 17/0293* (2013.01); *A61B 2017/00862* (2013.01); *A61B 2017/0287* (2013.01)

(58) Field of Classification Search
CPC .................. A61B 17/0231; A61B 2017/00867
See application file for complete search history.

(56) References Cited

U.S. PATENT DOCUMENTS

| 4,037,589 A | 7/1977 | McReynolds |
| 4,321,916 A | 3/1982 | McKee |

(Continued)

FOREIGN PATENT DOCUMENTS

| WO | WO2012037550 | * | 9/2011 | ............... A61F 9/00 |
| WO | 2014132264 A1 | | 9/2014 | |
| WO | 2014156586 A1 | | 10/2014 | |

OTHER PUBLICATIONS

Australian Patent Examination Report No. 1 for related/counterpart Australian Patent Application No. 2013380203, dated Sep. 14, 2016.

(Continued)

*Primary Examiner* — Samuel Hanna
(74) *Attorney, Agent, or Firm* — Greenberg Traurig LLP (57) ABSTRACT

A device, providing enlargement and preventing collapse, of the pupil of the eye, during an ophthalmic surgical procedure. The device, configured as a continuous or discontinuous ring, comprises plurality of notches at corners and flanges at sides. The ring is formed from a strand of resiliently flexible material and is disposed entirely within a single plane. The notches engage the pupillary margin at different parts, pushing them apart, resulting in sustained enlargement of the pupil. In addition, the device causes bending of the pupillary margin and iris at the notches and above and below the flanges, resulting in a secure engagement. The enlarged pupil created by the ring, allows a wide view of the structures deeper to the pupillary plane, previously obscured due to a small pupil.

13 Claims, 8 Drawing Sheets

(56) References Cited

U.S. PATENT DOCUMENTS

| | | |
|---|---|---|
| 4,782,820 A | 11/1988 | Woods |
| 5,163,419 A | 11/1992 | Goldman |
| 5,267,553 A | 12/1993 | Graether |
| 5,299,564 A | 4/1994 | Sabatino |
| 5,441,045 A | 8/1995 | Federman |
| 6,620,098 B1 | 9/2003 | Milverton |
| 6,648,819 B2 | 11/2003 | Lee |
| 8,323,296 B2 | 12/2012 | Malyugin |
| 8,496,583 B1 * | 7/2013 | Reynard ............ A61B 17/0231 600/235 |
| 2008/0108879 A1 | 5/2008 | Brown |
| 2008/0243139 A1 | 10/2008 | Dusek |
| 2012/0232351 A1 | 9/2012 | Assia et al. |
| 2012/0289786 A1 | 11/2012 | Dusek |
| 2013/0096386 A1 | 4/2013 | Christensen et al. |
| 2013/0131458 A1 * | 5/2013 | Malyugin ................ A61B 1/32 600/236 |
| 2013/0267988 A1 | 10/2013 | Sussman et al. |
| 2014/0221759 A1 | 8/2014 | Mackool et al. |
| 2014/0276900 A1 * | 9/2014 | Cote ................... A61F 9/00736 606/107 |
| 2014/0378773 A1 | 12/2014 | Dykes |
| 2015/0065809 A1 | 3/2015 | Assia et al. |
| 2015/0080665 A1 | 3/2015 | Cote et al. |
| 2015/0164685 A1 | 6/2015 | Bhattacharjee |

OTHER PUBLICATIONS

Search Report issued by the Intellectual Property Office of Singapore, regarding related/counterpart Singapore Patent Application No. 11201508026R, completed Apr. 14, 2016.
First Written Opinion of the Intellectual Property Office of Singapore, regarding related/counterpart Singapore Patent Application No. 11201508026R, dated Jun. 14, 2016.
Second Written Opinion of the Intellectual Property Office of Singapore, regarding related/counterpart Singapore Patent Application No. 11201508026R, dated Dec. 7, 2016.
Examination Report issued by the Intellectual Property of Singapore, regarding related/counterpart Singapore Patent Application No. 11201508026R, dated May 4, 2017.

* cited by examiner

PRIOR ART

Fig. 1

PRIOR ART

Fig. 2

PRIOR ART

Fig. 3

PRIOR ART

DEVICE PROVIDING ENLARGEMENT AND PREVENTING COLLAPSE OF THE PUPIL OF THE EYE

CROSS REFERENCE TO RELATED APPLICATION

This application claims priority to Application 225/KOL/2013 filed at Patent Office, India (IN), on Feb. 27, 2013.

BACKGROUND OF THE INVENTION

The present invention is in the field of ophthalmic surgery and relates to an improvement in the device for mechanical enlargement or dilation of the pupil of the eye during surgery.

During phacoemulsification surgery and vitreo-retinal surgery, when the pupil does not dilate with medicated drops, a device is required for mechanical enlargement of the pupil. Such a device has to maintain the pupil in the enlarged state and prevent it from collapsing for the entire duration of the surgery. Removal of the device returns the pupil to an unenlarged state to preserve its function and cosmesis. Eyes with non-dilating pupils are often also associated with floppiness of the iris, which poses additional difficulty during surgery.

In phacoemulsification surgery for cataract, a 1.6 to 2.8 mm incision in the side of the cornea is required to insert a phaco probe. Smaller incisions result in secure and astigmatically neutral wounds translating into better visual outcomes.

Vitreo-retinal surgery requires 0.6 mm or smaller incisions in the sclera to insert instruments into the eye. Since a corneal incision is not required, such an incision, only to insert a pupil-dilating device, should be as small as possible.

Current devices in use for pupillary dilation require a 2.2 to 2.5 mm incision for insertion into the eye. They snag the incision because of gaps or pockets at the corners, which have a biplanar structure with a top and bottom part. Such snagging makes removal of the device difficult and causes damage to the cornea. They require precise alignment to engage the pupillary margin into the small narrow wedge shaped gaps or pockets at the corners. This is particularly difficult because the surgeon has a top view and the device itself obscures view of the narrow gap, which is at the side of the device. The gaps or pockets have two structural planes having an upper and lower part making the corners thick and bulky. The gaps or pockets hold the pupillary margin and iris tissue passively and the pupillary margin can easily disengage during surgical manipulations.

Such continuous ring devices have been disclosed in U.S. Pat. No. 8,323,296, Dec. 4, 2012 by Malyugin, US Patent Application publication 2012/0269786, Nov. 15, 2012 by Dusek and US Patent Application publication 2013/0096386, Apr. 18, 2013 by Christensen & Colvard.

Though discontinuous ring devices have been disclosed in U.S. Pat. No. 5,163,419, Nov. 17, 1992 by Goldman, U.S. Pat. No. 5,267,553, Dec. 7, 1993 by Graether, U.S. Pat. No. 6,620,098, Sep. 16, 2003 by Milverton and U.S. Pat. No. 6,648,819, Nov. 18, 2003 by Lee, these devices have not found acceptance because of larger incision size required, cumbersome manipulations involved and loose engagement.

Objects of the Invention

The principal object of the present invention is to provide a device to enlarge the pupil of the eye, which requires a very small incision for insertion into the eye. Another object of the invention is to provide a device with a mechanism to engage the pupillary margin that will not snag the incision during insertion or removal. A further object of the invention is to provide a device, with an easier mechanism to engage the pupillary margin that does not require precise alignment of the pupillary margin into the narrow wedge shaped gaps or pockets at the sides of the device. A further object of the invention is to provide a device, with corners that can engage the pupillary margin but are slim and strictly in the same plane of the device. A further object of the invention is to provide a device, which not only enlarges the pupil, but also remains securely, yet reversibly fastened to iris tissue so that surgical manipulations do not lead to its disengagement. A further object of the invention is to provide a device that reduces floppiness of the Iris, which is often associated with non-dilating pupils.

SUMMARY OF THE INVENTION

The present invention is a device to enlarge and prevent collapse, of the pupil of the eye, during surgery. The notches and flanges, on the same plane of a continuous or discontinuous ring, used to engage the pupillary margin, is the novelty of the present invention. The notches are at corners and alternate with side elements or flanges along the perimeter of the ring. The notches are open outwards with a blind receptacle inwards. Notches engage different parts of the pupillary margin and push them apart, resulting in sustained enlargement of the pupil. The flanges are formed from broad loops of the strand and are directed outwards.

The device is made of a strand of any resiliently flexible material. Thermally treated 4-0 nylon suture (0.15 to 0.17 mm) is such. Notches temporarily straighten as they pass through the incision allowing the device to be inserted through a very small incision. The device, having no gaps or pockets, being entirely disposed in a single plane, passes through the incision without snagging. The device bends the pupillary margin and iris at the notches and flanges, somewhat like a paper clip, creating a secure engagement. The iris being flexible, can tolerate such bending without any damage. The flanges lying in front of the iris reduce its floppiness by restricting the billowing effect.

Within the scope of the same inventive concept, variations in design are necessary, to allow the surgeon choices depending on the nature of the surgery, size of the eye, depth of the anterior chamber, associated co morbidity, size of incision, initial pupil size, desired pupil size etc. Variations in design are also necessary to suit different manufacturing capabilities.

The continuous form of the ring is in the form of a polygon with at least three sides and can be with or without a joint. The ends are joined by knotting or tying of the ends, or by chemical, thermal or ultrasonic bonding of the ends or by any other method. When made by molding, stamping or other methods there is no joint. The discontinuous form of the ring has at least three sides, two corners and four notches. This form requires a much smaller incision for insertion.

In one of the form of the invention, the ring has alternate side elements or flanges gently tilted backwards, enabling easy tucking of the flange under the iris.

Notches are formed by an inward loop of the strand at the corners or by an inward loop of the strand between two outward digit shaped protruded loops of the strand. In one form of the invention, the corners of the ring have two adjacent notches.

Positioning holes on the device help in manipulations of the device. When the device is made of expansible material, it enlarges to a larger size after insertion.

The ring device is configured to adapt one or more selected configurations from a folded, extended or deformed configuration, allowing insertion through small incisions.

DETAILED DESCRIPTION OF DRAWINGS

The relevant features of existing devices and the novelty of the present invention, is illustrated in the accompanying drawings, throughout which, like reference numerals indicate corresponding parts in the various figures.

Figure 1:
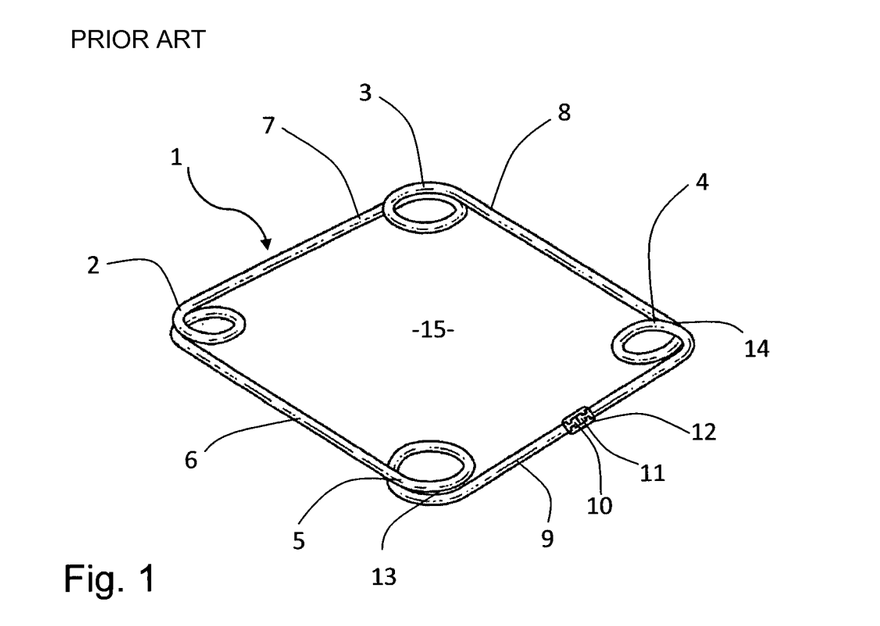
FIG. 1 is an enlarged diagrammatic top perspective of the ring of the type disclosed in Malyugin U.S. Pat. No. 8,323,296, Dec. 4, 2012.

FIG. 1 shows an enlarged diagrammatic top perspective of the ring of the type disclosed in Malyugin U.S. Pat. No. 8,323,296, Dec. 4, 2012. The Malyugin ring 1 has a square configuration with four helical loops 2, 3, 4 and 5 formed by one complete turn of the strand and separated by sides 6, 7, 8 and 9. The two ends 10 and 11, of the ring have indented portions and are butt attached to each other by adhesive at the joint 12. Each loop has a wedge shaped gap 13 and 14, which faces the periphery of the ring, to receive and capture the iris tissue. The ring 1 maintains the pupil in an extended position while the central opening 15 provides a wide viewing area during surgery.

Figure 2:
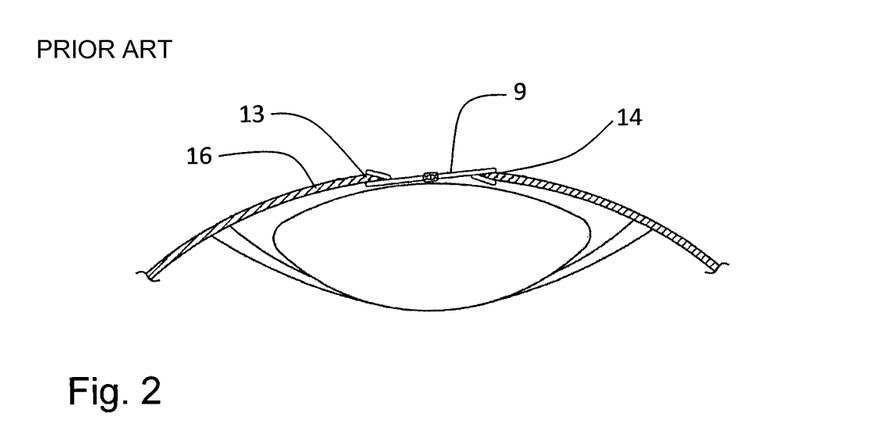
FIG. 2 is an enlarged diagrammatic side view of ring of the type disclosed in Malyugin U.S. Pat. No. 8,323,296, showing iris tissue within the wedge shaped gaps of the loops.

FIG. 2 shows an enlarged diagrammatic side view of ring of the type disclosed in Malyugin U.S. Pat. No. 8,323,296, showing iris tissue 16 within the wedge shaped gaps 13 and 14 of the loops. The side 9 connects the bottom part of gap 13, which is at one plane, to the top part of gap 14, which is at another plane.

Figure 3:
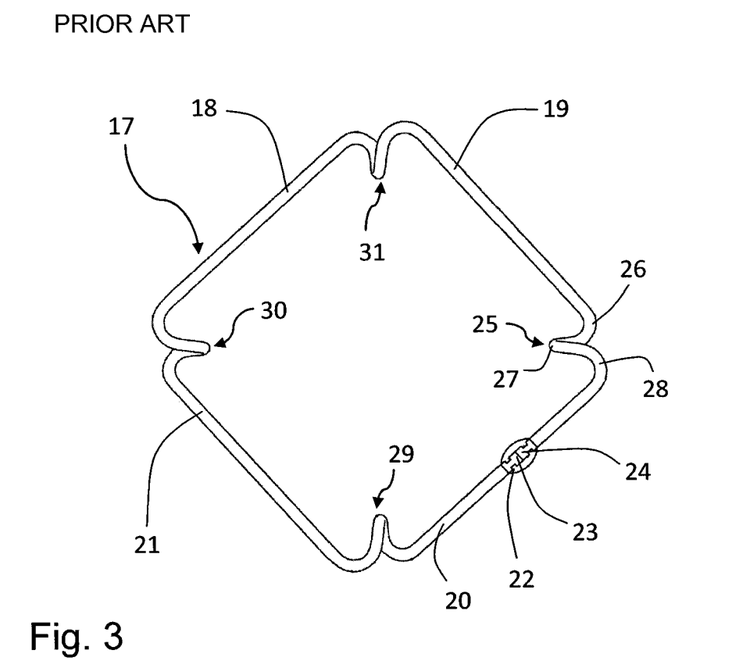
FIG. 3 is an enlarged diagrammatic top plan of the modified ring of the type disclosed in Dusek US Patent Publication 2012/0269786.

FIG. 3 shows an enlarged diagrammatic top plan of the modified ring of the type disclosed in Dusek US Patent Publication 2012/0269786. The Dusek ring 17 has four sides 18, 19, 20 and 21. Side 20 has the end butt joint 22 where a drop of adhesive secures the ends 23 and 24. Side 19 is perpendicular to side 20. The sides are joined by a corner portion 25 which has three distinct bends, namely, a first obtuse bend 26 (essentially 135° inward and to the left as viewed in FIG. 3), second return bend 27 (essentially 180° inward and then down away from the viewer and then toward the right as viewed in FIG. 3), and a third obtuse bend 28 (essentially 135° up and to the left as viewed in FIG. 3). Corner portions 29, 30 and 31 are identical to corner portion 25.

Figure 4:
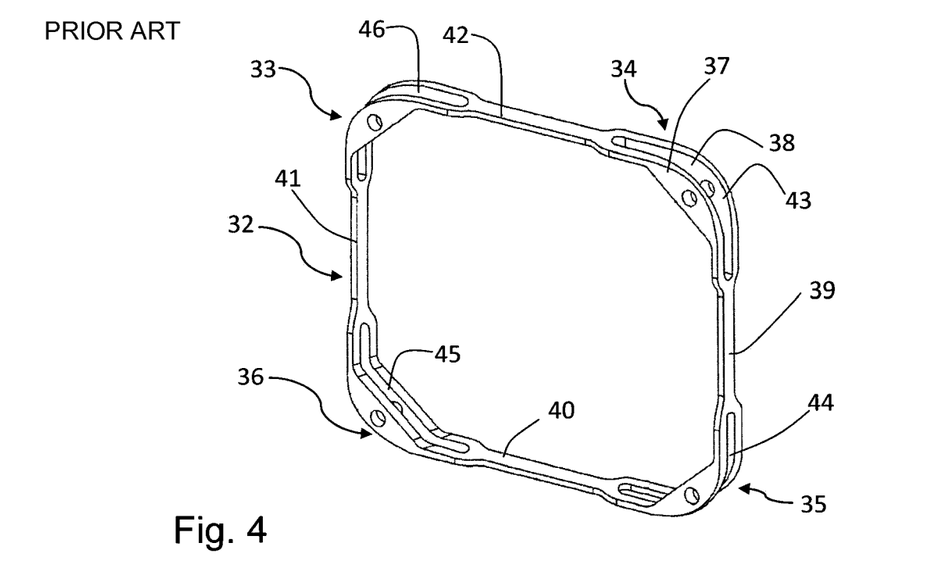
FIG. 4 is a perspective view of the ring of the type disclosed in Christensen & Colvard US Patent Publication 2013/0096386.

FIG. 4 shows a perspective view of the ring of the type disclosed in Christensen & Colvard US Patent Publication 2013/0096386. In the described embodiment of this disclosure, ring 32 has a square formation with rounded corners 33, 34, 35 and 36. At each corner, there is a top plate 37, which forms generally one plane of the ring and there is a bottom plate 38, which forms generally a second plane of the ring. These planes are generally above and below the primary plane of the ring formed by connecting limbs 39, 40, 41 and 42. Together, the outer periphery of the top plate and the bottom plate at each corner form a lip feature, which is the entrance of the pockets 43, 44, 45, and 46 that contain a portion of the iris, which is supported in an open configuration.

Figure 5:
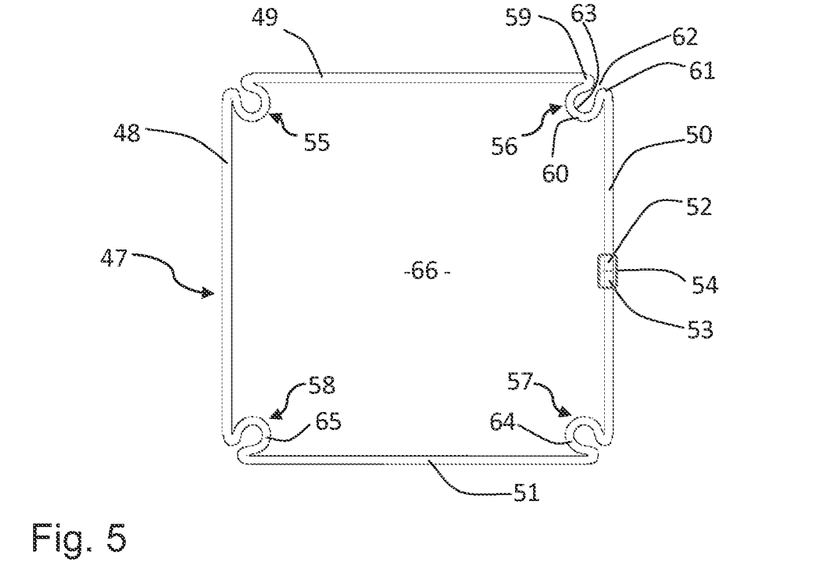
FIG. 5 is an enlarged diagrammatic top view of one form of the device of the present invention, showing a square shaped continuous ring with a joint.

FIG. 5 shows an enlarged diagrammatic top view of the ring of the present invention used for enlargement and prevention of collapse of the pupil. The ring 47 is made of any resiliently flexible strand, for example, thermally treated 4-0 nylon suture. It is a continuous ring, has a square configuration and has four sides 48, 49, 50 and 51, joined by corner portions. Side 50 has ends 52 and 53 joined at the butt joint 54 with adhesive. Each one of the corner portions 55, 56, 57 and 58, forms a notch, same numerals representing the notches. Corner portion 56 joins side 49 to side 50, which are perpendicular to each other. At the corner portion 56, the strand loops inwards to form a notch. Three distinct bends of the strand in the same plane form the notch. A first acute bend 59, second rounded return bend 60, and a third acute bend 61. The notch has a narrow outward opening 62, which allows iris tissue to enter the notch. Inwards, the notch has a blind, bulbous receptacle 63, which engages the pupillary margin and iris tissue gently. Corner portions 55, 57 and 58 are identical to corner portion 56. Parts 64 and 65 of corner portions 57 and 58 respectively, along with side 51, form an outward flange. Sides 48, 49 and 50, form similar flanges. The ring comprises alternate notches and flanges, all being in the same plane and enclosing a space 66.

Figure 6:
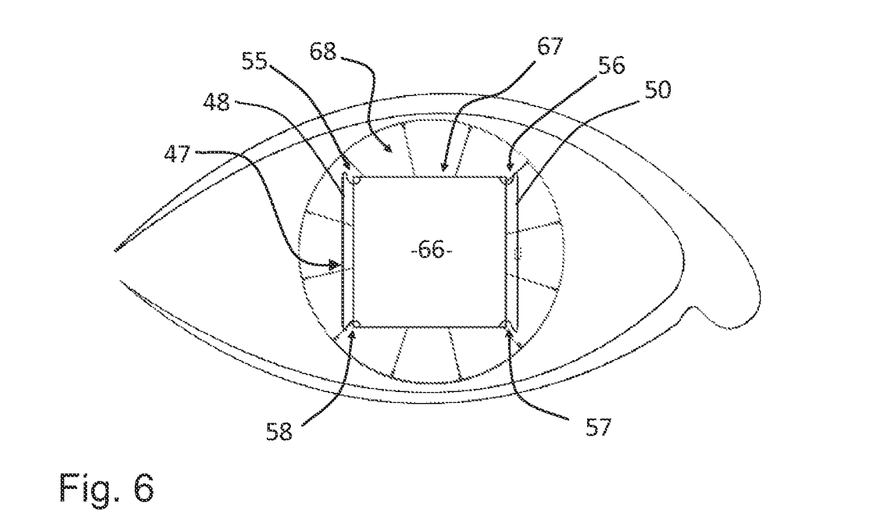
FIG. 6 is an illustration of pupil maintained in an enlarged position by the device of FIG. 5.

FIG. 6 shows an illustration of the pupil maintained in an enlarged position by the ring 47 of FIG. 5. The notches at corners 55, 56, 57 and 58, engage the pupillary margin 67 at different parts and push them apart, causing enlargement of the pupil. The flanges at sides 48 and 50 remain in front of the Iris 68. The flanges at sides 49 and 51 remain behind the Iris and are not visible. The alternate notches and flanges cause bending of the pupillary margin and iris tissue somewhat like a paper clip. This results in a secure yet reversible engagement. The central opening 66, allows wide view of the structures deeper to the pupillary plane.

Figure 7:
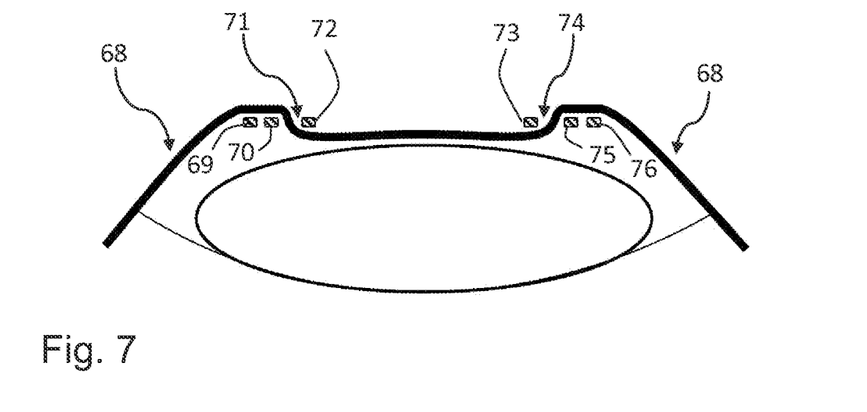
FIG. 7 is an enlarged diagrammatic side view showing the relation of iris tissue to the notches.

FIG. 7 shows an enlarged diagrammatic side view of the relation of iris tissue to the notches. This side view is at a vertical plane passing through the middle of any two adjacent notches of FIG. 6. The device distinctly bends the iris tissue 68, four times, as it passes through the two notches. From the left as viewed in FIG. 7, the iris 68 passes above the side element 69 and outer limb 70 of the notch 71. The first bend is at an obtuse angle as it passes downwards around the outer limb 70 of the notch 71 and through the notch. The second bend is at an obtuse angle to pass under the inner limb 72 of the notch 71. Iris 68 then makes a third bend at an obtuse angle as it passes upwards around the inner limb 73 of the notch 74 and through the notch. The final fourth bend is at an obtuse angle to pass above the outer limb 75 of the notch 74 and side element 76. As viewed in FIG. 7, side element 69, outer limb 70 of the notch 71, the notch 71, inner limb 72 of the notch 71, inner limb 73 of the notch 74, the notch 74, outer limb 75 of the notch 74 and side element 76, all lie in the same plane.

Figure 8:
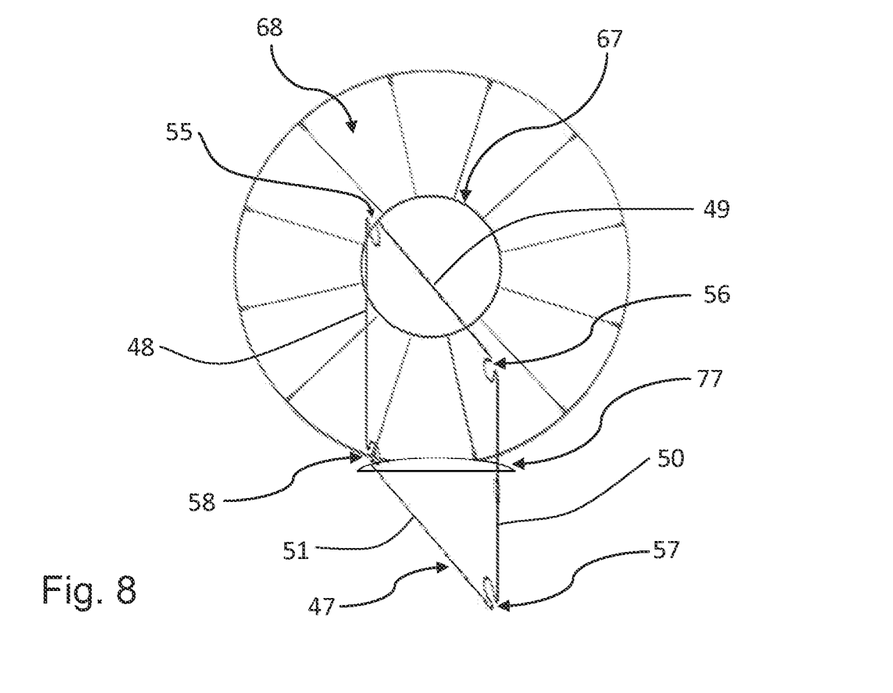
FIG. 8 is an illustration of the insertion of the ring device into the eye and engagement of the pupillary margin with the first notch of the device of FIG. 5.

FIG. 8 refers to the usage of the invention, is an illustration of the insertion of the ring 47 of FIG. 5, into the eye and engagement of the pupillary margin 67 with the first notch 55 of the ring. A forceps (not shown here) carries the device or an injector (not shown here) delivers the device through the incision 77, into the anterior chamber of the eye. The flexible square ring 47 adopts a rhomboid configuration as it negotiates through a much smaller incision 77. The notches 56 and 58 open up and temporarily straighten out as the device passes through the incision. The leading first notch 55 hooks and engages the pupillary margin 67 pushing it in an outward direction. The pupillary margin 67 is lifted with a Hirschman hook (not shown here) to tuck the flange 49 under the pupillary 67 and iris 68.

Figure 9:
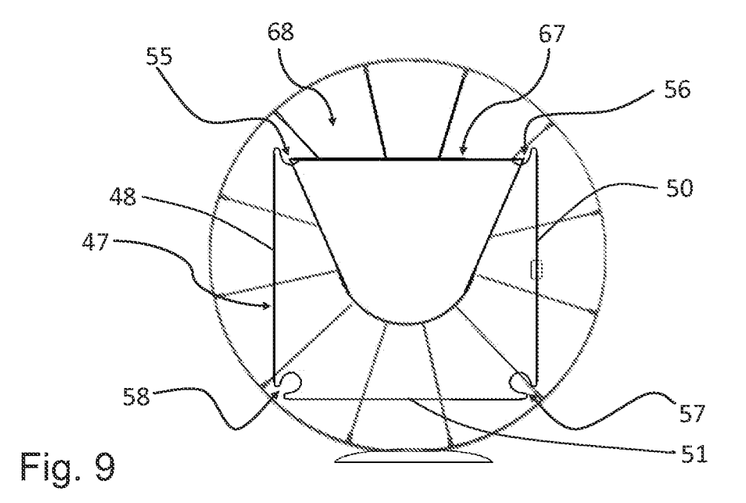
FIG. 9 is an illustration of the stretched pupillary margin after engagement by the second notch of the device of FIG. 5.

FIG. 9 refers to the sage of the invention in further detail, is an illustration of the stretched pupillary margin after engagement by the second notch 56 of the device 47 of FIG. 5. The resiliently flexible ring 47 has now returned to its square configuration. Notches 55 and 56 have engaged the pupillary margin 67 at two different points and pushed them apart. Flange 49 (not visible here), remains tucked under the pupillary margin 67, while flanges 48, 50 and 51, remain in front of the iris 68. As the pupillary margin is hooked again with an iris or hirschman hook, introduced through a side port (not shown here), a forceps introduced through another side port (not shown here), holds the flange 51 and tucks it under the pupillary margin 67 and iris 68.

Figure 10:
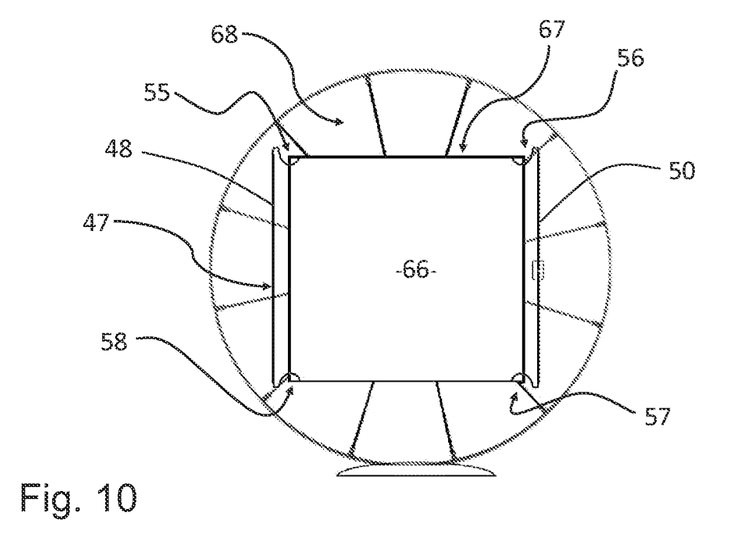
FIG. 10 is an illustration of the pupil fully enlarged after engagement by all four notches of the device of FIG. 5.

FIG. 10 refers to the usage of the invention in further detail, is an illustration of the pupillary margin 67, fully enlarged and adopting a square configuration after engagement by all four notches 55, 56, 57 and 58 of the device 47 of FIG. 5. The flanges 48 and 50 remain in front of the Iris 68. The flanges at sides 49 and 51 remain behind the iris and are not visible. The central opening 66, allows wide view of the structures deeper to the pupillary plane. On completion of surgery, the device is easily disengaged from the pupillary margin and pulled out with a forceps. The device exits the eye without snagging the incision because notches are in the same plane as the flanges and are capable of straightening temporarily.

Figure 11:
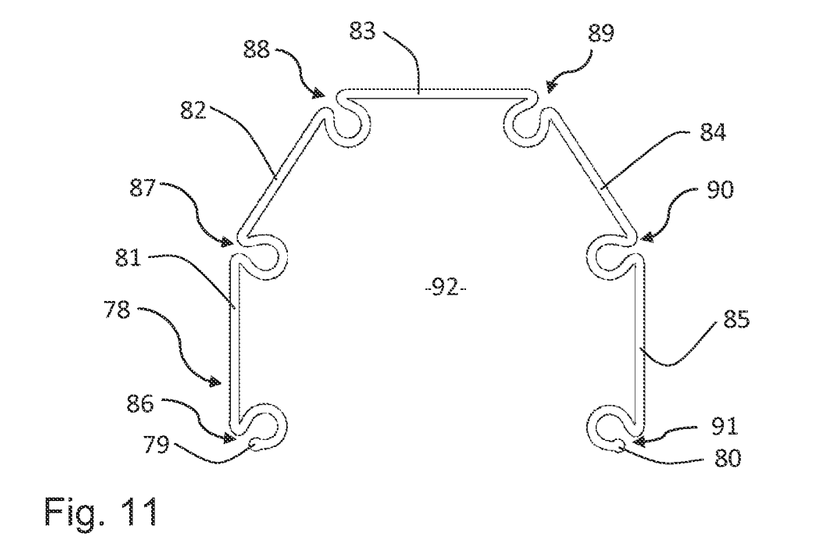
FIG. 11 is an enlarged diagrammatic top view of one form of the device of the present invention, showing a discontinuous ring with five sides, four corners and six notches.

FIG. 11 is an enlarged diagrammatic top view of another form of the device of the present invention, showing a discontinuous ring 78 with ends 79 and 80, which are blunt or olive shaped to prevent damage to delicate structures of the eye. The discontinuous ring 78 has five sides 81, 82, 83, 84 and 85, which are shaped like flanges. Corner portions joining these sides are internally obtuse angled. The four corner portions 87, 88, 89 and 90, form four notches, same numerals representing the notches. Notch 86 is at the first end and notch 91 is at the second end of the ring. In the device of FIG. 11, the angles at corner 87 and 90 are equal to each other and the angles at corner 89 and 90 are equal to each other. The first side 81 and the fifth side 85 are parallel to each other, giving the device a flat top house shape. The central space 92, is closed on five sides by the device, and open on one side. In another form of the device of FIG. 11 (not shown here), the first side 81 and the fifth side 85, are unparallel, such that the distance between the ends 79 and 80, is more than that between the first corner 87 and fourth corner 90, giving the device the shape of a flat top tower.

Figure 12:
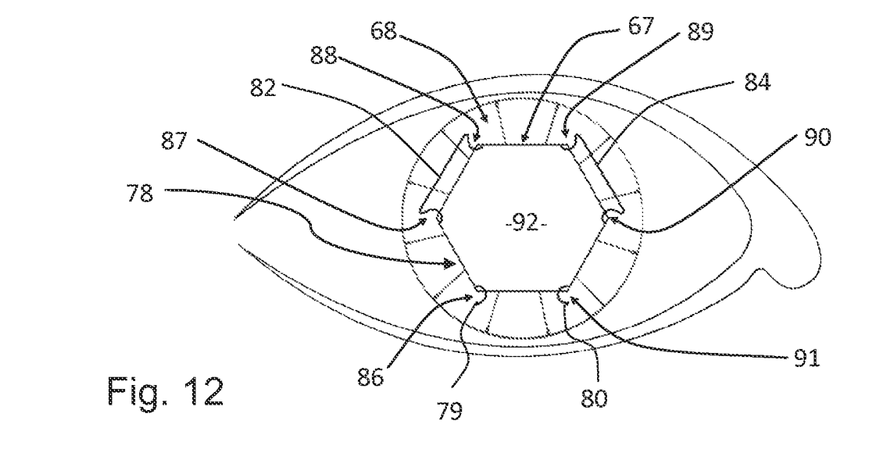
FIG. 12 is an illustration of the pupil maintained in an enlarged position by the device of FIG. 11.

FIG. 12 is an illustration of the pupil maintained in an enlarged position by the device of FIG. 11. The notches 86, 87, 88, 89, 90 and 91, engage the pupillary margin 67 at different parts and push them apart, causing enlargement of the pupil. Ends 79 and 80, and flanges 82 and 84 remain in front of the Iris 68. The flanges 81, 83 and 85 remain behind the Iris and are not visible. The constricting force of the pupil draws the notches at the ends 79 and 80 of the discontinuous ring closer and the resultant shape of the central space 92 of the device and that of the pupil is a hexagon. The central space 92, allows wide view of the structures deeper to the pupillary plane. While the device of FIG. 11 may be inserted into the eye, in the manner described above for the device of FIG. 5, the device may alternatively be inserted end first, into the eye, through a much smaller side port incision. The entire device is inserted into the anterior chamber and placed on the iris. The pupillary margin is hooked with an iris or hirschman hook, introduced through one side port incision, while a forceps introduced through another side port, holds flange 83 and tucks it under the pupillary margin 67. Similarly, flanges 81 and 85 are tucked under the pupillary margin.

Figure 13:
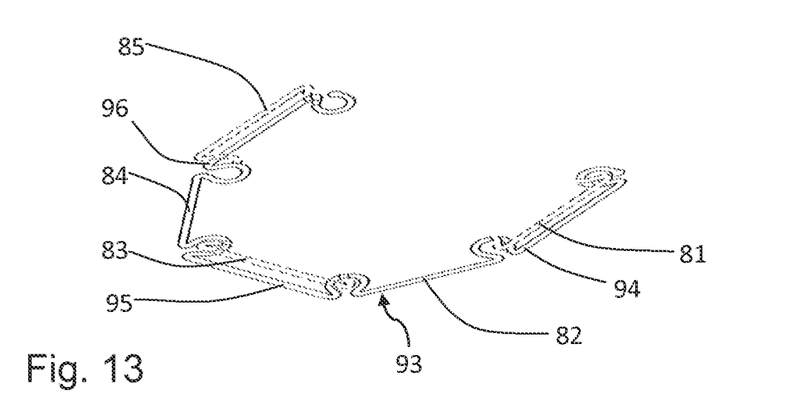
FIG. 13 is an enlarged diagrammatic top perspective of one form of the device of the present invention, showing alternate flanges of the device of FIG. 11, gently tilted backwards.

FIG. 13 is an enlarged diagrammatic top perspective of one form of the device of the present invention, showing alternate flanges of the device of FIG. 11, gently tilted backwards. Device 93 allows easier tucking of the flanges under the pupillary margin. Flanges 81, 83 and 85, shown in dotted lines, represent the previous straight position of flanges. Flanges 94, 95 and 96 represent the backward tilted flanges, respectively. The flanges are tilted all the way up to the centre of the notch or only at the peripheral edge. The position of flanges 82 and 84, which remain in front of the pupillary margin, is unaltered. Although tilted flanges are shown on the device of the present invention of FIG. 11, it is understood that such flanges may be present on all the forms of the device.

Figure 14:
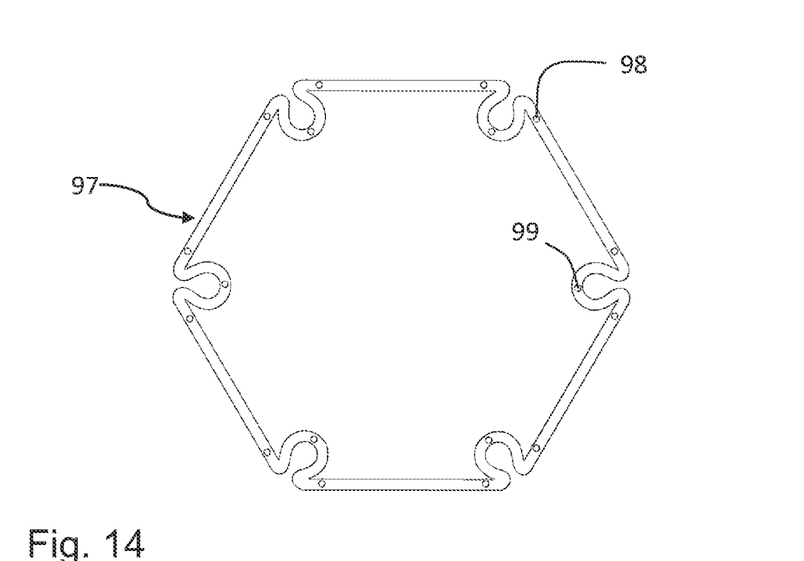
FIG. 14 is an enlarged diagrammatic top view of one form of the device of the present invention, showing plurality of positioning holes on a hexagon shaped continuous ring with no joint.

FIG. 14 is an enlarged diagrammatic top view of one form of the device of the present invention, showing plurality of positioning holes on a hexagon shaped continuous ring with no joint. Holes 98 and 99 are shown on a flange and notch respectively on the device 97. These holes are partial thickness or full thickness. These holes allow easy manipulation of the device inside the eye with the help of a pointed instrument called dialler. Although positioning holes or eyelets are shown on the device of the present invention of FIG. 14, it is understood that such positioning holes or eyelets may be present on all the forms of the device.

Figure 15:
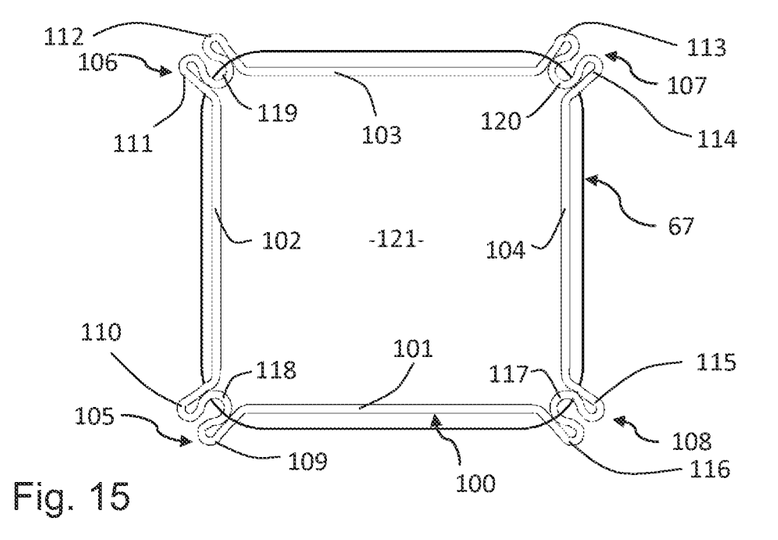
FIG. 15 is an enlarged diagrammatic top view of one form of the device of the present invention, showing engagement of the pupillary margin by notches formed by an inward loop of the strand between two outward digit shaped protruding loops of the strand of a square shaped continuous ring with no joint.

FIG. 15 is an enlarged diagrammatic top view of one form of the device of the present invention, showing engagement of the pupillary margin 67 by notches formed by an inward loop of the strand between two outward digit shaped protruding loops of the strand of a square shaped continuous ring with no joint. The ring 100 has four side elements 101, 102, 103 and 104. Corner portions 105, 106, 107 and 108, join the side elements. Corner portion 108 joins side 101 to side 104, which are perpendicular to each other. At the corner portion 108, the strand makes three distinct loops in the same plane to form a notch. Loops 115 and 116 are outward digit like protrusions. Notch 117, is formed by an inward loop between these two outward looped protrusions. Corner portions 105, 106 and 107 are identical to corner portion 108 and form notches 118, 119 and 120 respectively. The pupillary margin 67 has a square configuration as it is engaged by the notches 117, 118, 119 and 120, as it passes behind the elements 110, 111, 114 and 115, and in front of elements 112, 113, 116 and 109. The enclosed space 121, allows wide view of the structures deeper to the pupillary plane.

Figure 16:
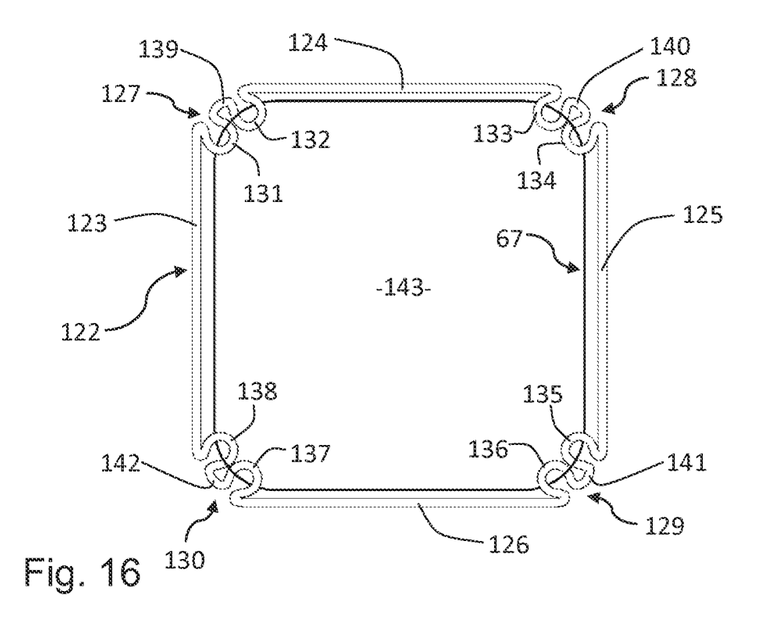
FIG. 16 is an enlarged diagrammatic top view of one form of the device of the present invention, showing engagement of the pupillary margin by two adjacent notches at the corners of a square shaped continuous ring with no joint.

FIG. 16 is an enlarged diagrammatic top view of one form of the device of the present invention, showing engagement of the pupillary margin 67 by two adjacent notches at the corners of a square shaped continuous ring with no joint. The ring 122 has four side elements 123, 124, 125 and 126. Corner portions 127, 128, 129 and 130, join the side elements. Corner portion 127 joins side 123 to side 124, which are perpendicular to each other. At the corner portion 127, the strand makes three distinct loops in the same plane to form two adjacent paired notches or a double notch. Paired notches 131 and 132 are formed by two loops directed inwards. A digit like structure 139, is formed between these two notches by a loop directed outwards. Corner portions 128, 129 and 130, are identical to corner portion 127 and form paired notches 133, 134 and 135, 136 and 137, 138 respectively. The pupillary margin 67 has a square configuration, engaged by the notches 131, 132, 133, 134, 135, 136, 137 and 138. The pupillary margin 67 passes behind side elements 123, 124, 125 and 126, and in front of elements 139, 140, 141 and 142. The enclosed space 143, allows wide view of the structures deeper to the pupillary plane. The pupillary margin 67 could alternately pass (not shown here) in front of side elements 123, 124, 125 and 126, and behind elements 139, 140, 141 and 142.

Those ordinarily skilled in the art can make changes in the embodiments described and illustrated, without altering the concepts of the present invention. Hence, it is to be understood that the invention is not limited to the descriptions, illustrations and examples, but includes all modifications within the scope of this invention.

The invention claimed is:

1. A device for enlarging a pupil of an eye during surgery, the eye including an iris and the pupil including a pupillary margin adjacent the iris, the device comprising:
 a closed ring formed from a single flexible strand, having a constant profile and degree of resiliency along its entirety,
 said closed ring enclosing a central space and having at least four straight co-planar flanges defining a plane, each of said at least four straight co-planar flanges being entirely contained within said plane before insertion into the eye, and after insertion into the eye, said at least four co-planar flanges including a first flange, a second flange, a third flange, and a fourth flange, and said ring further including:
 a first corner portion connectively disposed between said first flange and said second flange and forming first receiving means for receiving a first portion of the pupillary margin when inserted into the eye,
 a second corner portion connectively disposed between said second flange and said third flange and forming second receiving means for receiving a second portion of the pupillary margin when inserted into the eye, said first corner portion and said second corner portion extending into said central space such that said first and second receiving means open outwardly in a direction opposite to said central space,
 a third corner portion connectively disposed between said third flange and said fourth flange and forming third receiving means for receiving a third portion of the pupillary margin when inserted into the eye, and
 a fourth corner portion connectively disposed between said fourth flange and said first flange and forming fourth receiving means for receiving a fourth portion of the pupillary margin when inserted into the eye, said third corner portion and said fourth corner portion extending into said central space such that said third and fourth receiving means open outwardly in a direction opposite to said central space,
 said first corner portion including a first blind end within said central space, a first limb connecting said first flange to said first blind end on one side thereof, and a second limb connecting said second flange to said first blind end on an opposite side thereof so as to form said first receiving means, and wherein said first receiving means being a first notch sized and shaped to receive the first portion of the pupillary margin such that the iris passes over said first flange and said first limb and under said second limb and said second flange,
 said second corner portion including a second blind end within said central space, a third limb connecting said second flange to said second blind end on one side thereof, and a fourth limb connecting said third flange to said second blind end on an opposite side thereof so as to form said second receiving means, and wherein said second receiving means being a second notch sized and shaped to receive the second portion of the pupillary margin such that the iris passes under said second flange and said third limb and over said fourth limb and said third flange,
 said third corner portion including a third blind end within said central space, a fifth limb connecting said third flange to said third blind end on one side thereof, and a sixth limb connecting said fourth flange to said third blind end on an opposite side thereof so as to form said third receiving means, and wherein said third receiving means being a third notch sized and shaped to receive the third portion of the pupillary margin such that the iris passes over said third flange and said fifth limb and under said sixth limb and said fourth flange, and
 said fourth corner portion including a fourth blind end within said central space, a seventh limb connecting said fourth flange to said fourth blind end on one side thereof, and an eighth limb connecting said first flange to said fourth blind end on an opposite side thereof so as to form said fourth receiving means, and wherein said fourth receiving means being a fourth notch sized and shaped to receive the fourth portion of the pupillary margin such that the iris passes under said fourth flange and said seventh limb and over said eighth limb and said first flange, wherein said first, second, third and fourth flanges, said first, second, third and fourth corner portions, said first, second, third and fourth notches have a constant profile and degree of resiliency such that said first, second, third and fourth notches are entirely contained within said plane before insertion into the eye, and after insertion into the eye, wherein said first notch and said second notch are configured and positioned to push the first portion of the pupillary margin received in said first notch apart from the second portion of the pupillary margin received in said second notch to enlarge the pupil of the eye, and wherein said ring is moveable between an undeformed state before and after being inserted into the eye and a deformed state during insertion into the eye.

2. The device of claim 1, wherein said first blind end, said second blind end, said third blind end and said fourth blind end have a generally arcuate shape.

3. The device of claim 1, wherein said ring assumes a generally rectangular configuration when it is in its said undeformed state, and wherein said ring assumes a generally rhomboidal configuration when it is in its said deformed state.

4. The device of claim 3, wherein said generally rhomboidal configuration is selected so as to facilitate insertion of said ring into the eye.

5. The device of claim 1, wherein said ring is manually moveable from its said undeformed state to its said deformed state, and wherein said ring automatically returns to its said undeformed state from its said deformed state.

6. The device of claim 1, wherein said ring having at least four straight co-planar flanges further includes a straight co-planar fifth flange and a straight co-planar sixth flange, and wherein said ring further includes a fifth corner portion connectively disposed between said fifth flange and said sixth flange and forming fifth receiving means for receiving a fifth portion of the pupillary margin, and a sixth corner portion connectively disposed between said sixth flange and said first flange and forming sixth receiving means for receiving a sixth portion of the pupillary margin, said fifth corner portion and said sixth corner portion extending into said central space such that said fifth and sixth receiving means open outwardly in a direction opposite to said central space, said fifth corner portion including a fifth blind end, a ninth limb connecting said fifth flange to said fifth blind end on one side thereof, and a tenth limb connecting said sixth flange to said fifth blind end on an opposite side thereof so as to form said fifth receiving means, and wherein said fifth receiving means being a fifth notch sized and shaped to receive the fifth portion of the pupillary margin such that the iris passes over said fifth flange and said ninth limb and under said tenth limb and said sixth flange, said sixth corner portion including a sixth blind end, an eleventh limb connecting said sixth flange to said sixth blind end on one side thereof, and a twelfth limb connecting said first flange to said sixth blind end on an opposite side thereof so as to form said sixth receiving means, and wherein said sixth receiving means being a sixth notch sized and shaped to receive the sixth portion of the pupillary margin such that the iris passes under said sixth flange and said eleventh limb and over said twelfth limb and said first flange; and said fourth corner portion being connectively disposed between said fourth flange and said fifth flange, such that said seventh limb connecting said fourth flange to said fourth blind end on one side thereof, and said eighth limb connecting said fifth flange to said fourth blind end on an opposite side thereof so as to form said fourth receiving means, and wherein said fourth receiving means being a fourth notch.

7. The device of claim 6, wherein said first blind end, said second blind end, said third blind end, said fourth blind end, said fifth blind end and said sixth blind end have a generally arcuate shape.

8. The device of claim 6, wherein said fifth and sixth flanges, said fifth and sixth corner portions, said fifth notch and said sixth notch have a constant profile and degree of resiliency such that said fifth and sixth notches are entirely contained within said plane before insertion into the eye, and after insertion into the eye.

9. The device of claim 8, wherein said ring assumes a generally regular hexagonal configuration when it is in its said undeformed state, and wherein said ring assumes a generally nonregular hexagonal configuration when it is in its said deformed state.

10. The device of claim 9, wherein said generally nonregular hexagonal configuration is selected so as to facilitate insertion of said ring into the eye.

11. The device of claim 8, wherein said ring is manually moveable from its said undeformed state to its said deformed state, and wherein said ring automatically returns to its said undeformed state from its said deformed state.

12. The device of claim 1, wherein said second flange includes a first portion proximate said first corner portion and including a first end distal said first corner portion, a second portion proximate said second corner portion and including a second end distal said second corner portion, and a joint connectively disposed between said first end of said first portion and said second end of said second portion.

13. The device of claim 1, further comprising a plurality of positioning holes in said ring, each of said plurality of positioning holes being dimensioned to receive an instrument to facilitate manipulation of said ring within the eye.

* * * * *